United States Patent [19]

Farkas et al.

[11] B 4,017,472

[45] Apr. 12, 1977

[54] PROCESS FOR ISOLATION OF ASPARTYL DIPEPTIDE ESTERS

[75] Inventors: Walter G. Farkas, Ruvigliana, TI, Switzerland; Willard M. Hoehn, Cupertino, Calif.; Joseph F. Zawadzki, Skokie, Ill.

[73] Assignee: G. D. Searle & Co., Chicago, Ill.

[22] Filed: July 5, 1974

[21] Appl. No.: 485,972

[44] Published under the second Trial Voluntary Protest Program on March 23, 1976 as document No. B 485,972.

Related U.S. Application Data

[63] Continuation-in-part of Ser. No. 337,927, March 5, 1973, abandoned.

[30] Foreign Application Priority Data

Feb. 25, 1974 Canada .............................. 193344

[52] U.S. Cl. ....................................... 260/112.5 R
[51] Int. Cl.² .................. C07C 103/52; A23L 1/22

[58] Field of Search ................................ 260/112.5

[56] References Cited

UNITED STATES PATENTS

| 3,678,026 | 7/1972 | Ariyoshi et al. ................ 260/112.5 |
| 3,695,898 | 10/1972 | Hill et al. ........................ 260/112.5 |

FOREIGN PATENTS OR APPLICATIONS

| 2,040,473 | 1/1971 | France |
| 2,107,411 | 8/1971 | Germany |

*Primary Examiner*—Lewis Gotts
*Assistant Examiner*—Reginald J. Suyat
*Attorney, Agent, or Firm*—John J. Kolano

[57] ABSTRACT

The isolation of certain dipeptide esters, known to be potent sweetening agents, is achieved by selectively extracting, with a suitable alkanol in a heterogeneous system, an aqueous solution containing the dipeptide ester together with a variety of impurities.

9 Claims, No Drawings

PROCESS FOR ISOLATION OF ASPARTYL DIPEPTIDE ESTERS

This application is a continuation-in-part of our copending application Ser. No. 337,927, filed Mar. 5, 1973, and now abandoned.

The present invention relates to a novel and advantageous process for isolating certain dipeptide esters from crude mixtures thereof. The dipeptide esters contemplated have the general structural formula

wherein X is a phenyl or p-hydroxyphenyl radical, R is an alkyl radical containing 1 to 7 carbon atoms and the sterochemical configuration is L-L. These compounds are of interest as sweetening agents, as is disclosed in U.S. Pat. Nos. 3492131, 3475403 and 3714139. As is described in those patents, the dipeptide esters can be manufactured by reacting an aspartic acid derivative with the appropriate amino acid alkyl ester, then removing, if present, protecting groups attached to the amino and/or carboxy functions.

The alkyl radicals encompassed by R in the foregoing structural formula are typified by methyl, ethyl, propyl, pentyl, hexyl, heptyl and the branched-chain isomers thereof.

Preferred dipeptide esters of formula (I) whose isolation is especially contemplated by the present invention are L-α-aspartyl-L-phenylalanine methyl ester and L-α-aspartyl-L-tyrosine methyl ester.

Various procedures have been devised for the preparation of the dipeptide esters of formula (I) since their value as sweetening agents was first described. A preferred method for manufacture of the aforementioned dipeptide esters involves reaction of a strong acid salt of L-aspartic acid anhydride with the appropriate amino acid ester. As a specific example, L-aspartic acid anhydride hydrochloride is allowed to react with L-phenylalanine methyl ester in ethyl acetate or 1,2-dichloroethane. That anhydride salt is readily obtained by reaction of aspartic acid with phosphorous trichloride in a suitable alkanoic acid medium, e.g. propionic acid. After completion of the coupling reaction, the product is extracted with water; the pH of the aqueous extract is adjusted to the isoelectric point of the dipeptide ester; the unreacted amino acid ester is removed by extraction with a water insoluble organic solvent such as ethyl acetate; and the aqueous layer is concentrated to afford the crude product, which contains a variety of impurities, e.g. the corresponding β-dipeptide ester, the tripeptide formed by reaction of the dipeptide ester with another molecule of aspartic acid anhydride (i.e. α-aspartyl-aspartylphenylalanine methyl ester), the diketopiperazine formed by internal condensation of the dipeptide ester, free aspartic acid, α-aspartylphenylalanine and β-aspartylphenylalanine. These impurities are very difficult to remove. Purification and isolation of the desired dipeptide ester is typically achieved by laborious, time-consuming and expensive procedures such as fractional crystallization, ion exchange and electrodialysis.

It has recently been found that when a crude mixture containing L-α-aspartyl-L-phenylalanine methyl ester and the impurities formed in its manufacture (i.e., the β-dipeptide ester and other contaminants mentioned above) is recrystallized from an aqueous solvent containing hydrogen chloride or hydrogen bromide in excess with respect to the L-α-aspartyl-L-phenylalanine methyl ester, the L-α-aspartyl-L-phenylalanine methyl ester crystallizes out in the form of an acid-addition salt, substantially free of the corresponding β-isomer. Brithsh patent specification Nos. 1326473 and 1339101 describe this improvement in the isolation of L-α-aspartyl-L-phenylalanine methyl ester. Although the salt, e.g. L-α-aspartyl-L-phenylalanine methyl ester hydrochloride, remains contaminated with the other impurities mentioned above, its freedom from the β-isomer makes it a desirable material from which to isolate the desired dipeptide ester in accordance with the process of the present invention.

In contrast to the difficult and expensive isolation procedures which were heretofore necessary, it has surprisingly been discovered that the desired dipeptide ester is readily isolated from a crude mixture containing said dipeptide ester by employing an isolation procedure which includes the steps of partitioning the crude mixture between water and a suitable alkanol and isolating the dipeptide ester from the alkanol layer. The conditions of the partitioning step must be such that the alkanol solution separates as a discrete layer. It is thus apparent that alkanols with low water solubility such as n-butyl alcohol, isobutyl alcohol, sec.-butyl alcohol, tert.-butyl alcohol, n-amyl alcohol, sed.-amyl alcohol, isoamyl alcohol and tert.-amyl alcohol are especially preferred. Prior to the practice of the present process, the extracting alkanols are optionally equilibrated with aqueous inorganic salt solutions. Water soluble alkanols such as methanol, ethanol, n-propyl alcohol and isopropyl alcohol can be used also in combination with inorganic salts added to decrease the solubility of those alkanols in the aqueous layer. Suitable inorganic salts are sodium chloride, sodium sulfate, and sodium hydrogen diphosphate.

Particularly preferred alkanols for utilization in the present process are those which have, in addition to limited water solubility, also a relatively high degree of volatility. Those alkanols whose boiling points are near 100°C. are thus especially advantageous by virtue of the fact that they are readily removed, thus contributing to the convenience and economic advantage of the present process.

An especially preferred alkanol for use in the partitioning step is n-butyl alcohol. Also, the addition of methanol to the n-butyl alcohol/water system has been found to substantially enhance the extraction of the dipeptide ester into the n-butyl alcohol layer. The methanol can be added during preparation of the crude mixture which is to be partitioned, or it can be added to the crude mixture in combination with the water or n-butyl alcohol during the partitioning step.

The observation that the dipeptide esters can be extracted from aqueous solutions with the aforementioned alkanols is especially surprising in view of the fact that those esters, in their pure form, are not appreciably soluble in those alkanols. It is surprising also that the desired dipeptide esters along with a small amount of the undesired β-isomers (when β-isomers are present in the crude mixture being partitioned) are selectively extracted, leaving the aforementioned impurities, for the most part, in the aqueous layer. The β-isomer, if present, is readily removed by virtue of its greater solubility in the alkanol solution or, alternatively, by aqueous recrystallization.

The temperature at which the partitioning step is practiced is not critical, although the process can be conveniently conducted at about 20°–60°C. Similarly, the pH of the mixture during extraction need not be controlled, although the process is preferably carried out at or near the isoelectric point of the dipeptide ester.

Obviously, when the crude mixture containing the dipeptide ester is in the form of the dipeptide ester acid addition salt plus the impurities formed in its manufacture, then the dipeptide ester is regenerated, e.g. by neutralization of the dipeptide ester salt with a suitable base, prior to the partitioning step. The inorganic salt thus formed, e.g. sodium chloride, is removed during the partitioning step.

After partitioning, the desired dipeptide ester remaining in the alkanol layer is isolated. Isolation can be conveniently effected by partial concentration of the alkanol solution, followed by separation of the crystalline dipeptide ester thus formed. Alternatively, the alkanol layer can be concentrated to dryness and the partially purified product recrystallized from water. Isolation can be achieved also by azeotropic distillation of the alkanol layer with water followed by crystallization of the dipeptide ester from the aqueous layer.

As a result of the present invention, the dipeptide esters are obtained in a high degree of purity and in high yield. The laborious procedures previously necessary to effect such purification are thus avoided.

The invention will appear more fully from the examples which follow. In these examples, temperatures are given in degrees Centigrade (°C.).

EXAMPLE 1

To a suspension of 10 g. of L-aspartic acid in 40 ml. of propionic acid is added, at room temperature with stirring, 3.8 g. of phosphorous trichloride and stirring is continued at that temperature for about 1 ½ hours. At the end of that time, 5 g. of acetic anhydride is added and the reaction mixture is stirred at room temperature for approximately 8 hours longer. The crystals which separate from the reaction mixture are filtered, washed with ether and dried to afford L-aspartic acid anhydride hydrochloride.

EXAMPLE 2

To a suspension of 2 g. of L-aspartic acid in 10 ml. of propionic acid is added, at room temperature with stirring, 2.1 g. of phosphorous tribromide and stirring of the reaction mixture is continued for approximately 1 ½ hours. At the end of that time, 1.8 g. of acetic anhydride is added and stirring is continued at room temperature for approximately 7 hours. The crystalline product which separates is collected by filtration, washed with ether and dried, thus affording L-aspartic acid anhydride hydrobromide.

EXAMPLE 3

A suspension consisting of 10.8 g. of L-phenylalanine methyl ester hydrochloride, 200 ml. of ethyl acetate and 100 ml. of water is neutralized by the addition of 4.6 g. of sodium bicarbonate. The ethyl acetate layer is dried over anhydrous sodium sulfate, then concentrated to dryness under reduced pressure. The L-phenylalanine methyl ester thus obtained is dissolved in 100 ml. of ethyl acetate and 4.9 g. of L-aspartic acid anhydride hydrobromide is added at ⁻50°C. with stirring. Stirring is continued for about 40 minutes, at the end of which time the reaction mixture is extracted with water. The aqueous layer is separated and the pH adjusted to 4.8–5.0 by the addition of aqueous sodium carbonate. The aqueous solution is then extracted several times at 50°C. with n-butyl alcohol, which has been equilibrated with an aqueous sodium chloride solution, prepared by dissolution of 11.68 g. of sodium chloride in 1300 ml. of water. The alcohol extracts are combined, then concentrated to dryness under reduced pressure to afford the crude product. Recrystallization of that material from water affords L-$\alpha$-aspartyl-L-phenylalanine methyl ester.

EXAMPLE 4

The procedure of Example 3 is repeated, except that equilibration of the n-butyl alcohol with aqueous sodium chloride is omitted. By following the subsequent procedures described in Example 3, there is likewise obtained L-$\alpha$-aspartyl-L-phenylalanine methyl ester.

EXAMPLE 5

The procedure described in Example 3 is repeated and the aqueous extract of the reaction mixture, which has a pH of 5.6, is extracted with n-butyl alcohol directly at that pH. Following the subsequent procedures described in Example 3, there is thus obtained L-$\alpha$-aspartyl-L-phenylalanine methyl ester.

EXAMPLE 6

The procedure of Example 3 is repeated, using, as the extracting solvent, n-butyl alcohol which has been preequilibrated, as described in that Example, with aqueous sodium chloride. The extraction is carried out at room temperature rather than at 50°C. By following the subsequent procedures described in Example 3, there is thus obtained L-$\alpha$aspartyl-L-phenylalanine methyl ester.

EXAMPLE 7

When an equivalent quantity of L-aspartic acid anhydride hydrochloride is substituted in the procedure of Example 3 and the subsequent procedures described therein are followed, L-$\alpha$-aspartyl-L-phenylalanine methyl ester is obtained.

EXAMPLE 8

The substitution of an equivalent quantity of L-tyrosine methyl ester in the procedure of Example 3 results in L-$\alpha$-aspartyl-L-tyrosine methyl ester.

EXAMPLE 9

The procedure of Example 3 is repeated, wherein isopropyl alcohol is substituted for n-butyl alcohol and sodium chloride is added to the aqueous layer so that the concentration is approximately 11%, thus affording L-$\alpha$-aspartyl-L-phenylalanine methyl ester.

EXAMPLE 10

Phenylalanine methyl ester, prepared by neutralization of 43.0 g. of phenylalanine methyl ester hydrochloride, is combined with 375 ml. of 1,2-dichloroethane and 15 ml. of methanol. The resultant solution is cooled to ⁻20°C. with stirring and carbon dioxide gas is bubbled therethrough while maintaining the temperature at ⁻20°C. After approximately 15 minutes, 7.58 parts of L-aspartic acid anhydride hydrochloride is rapidly added. Stirring is continued for 1 ½ hours, and 175 ml. of hot water (approximately 65°C.) is then added. After 10 minutes, a solution of 2.85 g. of sodium carbonate monohydrate in 75 ml. of water is added to bring the pH to 5.9. The stirred mixture is then heated at 52° and the upper aqueous layer is held at pH 5.7 by the addition of 10% aqueous sodium carbonate monohydrate solution. The aqueous layer is thereupon extracted six times at 50°C. with 40 ml. portions of warm 1,2-dichloroethane. The 1,2-dichloroethane-extracted aqueous layer is evaporated at about 50°C. under reduced pressure until its weight is 174.6 g. and L-α-aspartyl-L-phenylalanine methyl ester is crystallizing.

The crystallizing evaporated aqueous mixture is extracted at 50°C. with n-butyl alcohol, once with a 150 ml. portion, then four times with 100 ml. portions. The combined n-butyl alcohol extracts are evaporated at about 65°C., with stirring, until white crystals form. Then the solid material is separated, washed with hot n-butyl alcohol and dried under reduced pressure at 35°C. to afford 10.13 g. of white solid. That solid is dissolved in a minimum of hot water and the hot mixture is then filtered and cooled at 0°C. for 4 ½ hours. The white crystals which form are collected, washed with ice water and dried at 56°C. under reduced pressure to a constant weight of 7.01 g. A second recrystallization from water affords pure L-α-aspartyl-L-phenylalanine methyl ester.

EXAMPLE 11

1270 G. of L-α-aspartyl-L-phenylalanine methyl ester hydrochloride [analyzing for 35.9% L-α-aspartyl-L-phenylalanine methyl ester, 0.9% aspartylphenylalanine, 2.6% α-aspartylaspartylphenylalanine methyl ester, a trace of aspartic acid, 1.2% diketopiperazine and 12.1% chloride ion] is added at room temperature to a mixture of 12 l. of water and 1260 ml. of methanol. The resultant mixture is adjusted to pH 3.0 by the addition of 10% aqueous sodium carbonate solution, then is heated to 50°. The pH is then adjusted to 4.78 by the addition of 10% aqueous sodium carbonate solution and 1.73 l. of water is added. There is thus obtained 18 l. of solution containing 454 g. of L-α-aspartyl-L-phenylalanine methyl ester, 4.33 moles of chloride, 6 g. of diketopiperazine, 5 g. of aspartylphenylalanine and 33.4 g. of α-aspartylaspartylphenylalanine methyl ester.

An approximately 5.08 cm. diameter Karr column is filled with equilibrated n-butyl alcohol. The above-prepared solution containing L-α-aspartyl-L-phenylalanine methyl ester is fed into the center of the Karr column at a rate of 8.28 kg./hour for 2 hours. At the same time, 7.1 kg. of 50°C. water is fed into the top of the column at a rate of 3.16 kg./hour and 53 kg. of 50°C. equilibrated n-butyl alcohol is fed into the bottom of the column at a rate of 21.6 kg./hour. Water is drawn off the bottom of the column as it accumulates and the n-butyl alcohol is allowed to overflow at the top of the column. At the end of approximately 2 ⅔ hours, reciprocation of the plates is stopped and the butyl alcohol and aqueous layers that form are separated and added, respectively, to the n-butyl alcohol and aqueous outputs from the column. There is obtained 55 kg. of n-butyl alcohol solution containing substantially all of the L-α-aspartyl-L-phenylalanine methyl ester present in the starting material, 0.07 mole chloride, 4 g. diketopiperazine, 0.7 g. aspartylphenylalanine and 5 g. α-aspartylaspartylphenylalanine methyl ester. The aqueous output weighs 22.6 kg. and contains 10 g. L-α-aspartyl-L-phenylalanine methyl ester, 3.91 moles chloride, 4 g. diketopiperazine, 3 g. aspartylphenylalanine and 28 g. α-aspartylaspartylphenylalanine methyl ester.

An 1103 g. aliquot of the latter n-butyl alcohol solution is azeotropically distilled with 1100 ml. of water. The remaining aqueous solution is diluted with water to a volume of 550 ml., then heated to 50°, decolorized with activated carbon, concentrated to a volume of 276 ml., and cooled at about 5° until crystallization is complete. The crystalline product is isolated by filtration, washed on the filter with water, then dried to afford 7.88 g. (84% yield) of L-α-aspartyl-L-phenylalanine methyl ester [analyzing for 101.3% L-α-aspartyl-L-phenylalanine methyl ester, trace of L-β-aspartyl-L-phenylalanine methyl ester, trace of diketopiperazine, 0.7% α-aspartylaspartylphenylalanine methyl ester, 0.02% residue on ignition, and 2.6% loss on drying].

What is claimed is:

1. In a process for preparing a dipeptide ester of the general formula

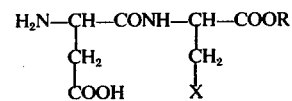

wherein X is a phenyl or p-hydroxyphenyl radical, R is an alkyl radical containing 1 to 7 carbon atoms and the stereochemical configuration is L-L; by the reaction of an L-aspartic acid anhydride salt with a compound of the formula

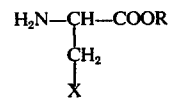

wherein R and X are defined as above, the step of isolating said dipeptide ester from the crude reaction mixture containing said ester which comprises partitioning said crude mixture between water and a suitable alkanol containing up to 5 carbon atoms and isolating the dipeptide ester from the alkanol layer.

2. A process according to claim 1 wherein the alkanol is n-butyl alcohol.

3. A process according to claim 1 wherein the alkanol is n-butyl alcohol and wherein methanol is added to the n-butyl alcohol/water system.

4. A process according to claim 1 wherein the partitioning step is carried out at approximately 50°C.

5. A process according to claim 1 wherein the partitioning step is carried out at room temperature.

6. A process according to claim 1 wherein the dipeptide ester is isolated by crystallization from the alkanol layer.

7. A process according to claim 1 wherein the dipeptide ester is isolated by azeotropic removal of the alkanol followed by crystallization from the resulting aqueous mixture.

8. A process according to claim 1 wherein the crude mixture is obtained by neutralization of crude L-α-aspartyl-L-phenylalanine methyl ester hydrochloride.

9. In a process for preparing L-α-aspartyl-L-phenylalanine methyl ester by the reaction of a L-aspartic acid anhydride salt with phenylalanine methyl ester, the step of isolating said dipeptide ester from a crude mixture containing said compound which comprises partitioning said crude mixture between water and a suitable alkanol containing up to 5 carbon atoms and isolating L-α-aspartyl-L-phenylalanine methyl ester from the alkanol layer.

* * * * *